United States Patent [19]

Jammet et al.

[11] Patent Number: 5,941,882
[45] Date of Patent: Aug. 24, 1999

[54] MEDICAL SCREW PARTICULARLY FOR SURGERY AND EMPLACEMENT TOOL

[75] Inventors: Jean Jammet, Objat; Jean-Pierre Lenfant, Rochechouart; Andre Peyre, Bordeaux, all of France

[73] Assignees: Societe Etudes et Developpements S.E.D., Voutezac; Multi-Poles Conseils, Rochechouart, both of France

[21] Appl. No.: 08/887,231

[22] Filed: Jul. 2, 1997

[30] Foreign Application Priority Data

Jul. 2, 1996 [FR] France .................................. 96 08442

[51] Int. Cl.⁶ .................................................. A61B 17/04
[52] U.S. Cl. .............................................. 606/73; 606/232
[58] Field of Search ........................... 606/72, 73, 139, 606/228, 232

[56] References Cited

U.S. PATENT DOCUMENTS

| | | |
|---|---|---|
| 5,002,550 | 3/1991 | Li . |
| 5,100,417 | 3/1992 | Cerier et al. ........................... 606/139 |
| 5,176,682 | 1/1993 | Chow . |
| 5,250,055 | 10/1993 | Moore et al. . |
| 5,324,308 | 6/1994 | Pierce . |
| 5,370,662 | 12/1994 | Stone et al. .............................. 606/232 |
| 5,443,482 | 8/1995 | Stone et al. . |
| 5,503,634 | 4/1996 | Christy . |
| 5,584,836 | 12/1996 | Ballintyn et al. ......................... 606/73 |
| 5,643,320 | 7/1997 | Lower et al. ............................ 606/232 |

FOREIGN PATENT DOCUMENTS 2 704 171  10/1994  France .
WO 93/15666  8/1993  WIPO .

*Primary Examiner*—Michael Buiz
*Assistant Examiner*—David O. Reip
*Attorney, Agent, or Firm*—Young & Thompson

[57] ABSTRACT

A medical screw adapted to be anchored in osseous material during surgery to secure a suture (26). The screw has a screw body (14) provided with a screw thread (16). Two longitudinal recesses (22) permit free passage of a suture (26) longitudinally in a loop below the screw. A transverse slot (18) receives the screwdriver blade of a tool to rotate the screw body. A quantity of suture is stored in and dispensed from the tool.

4 Claims, 4 Drawing Sheets

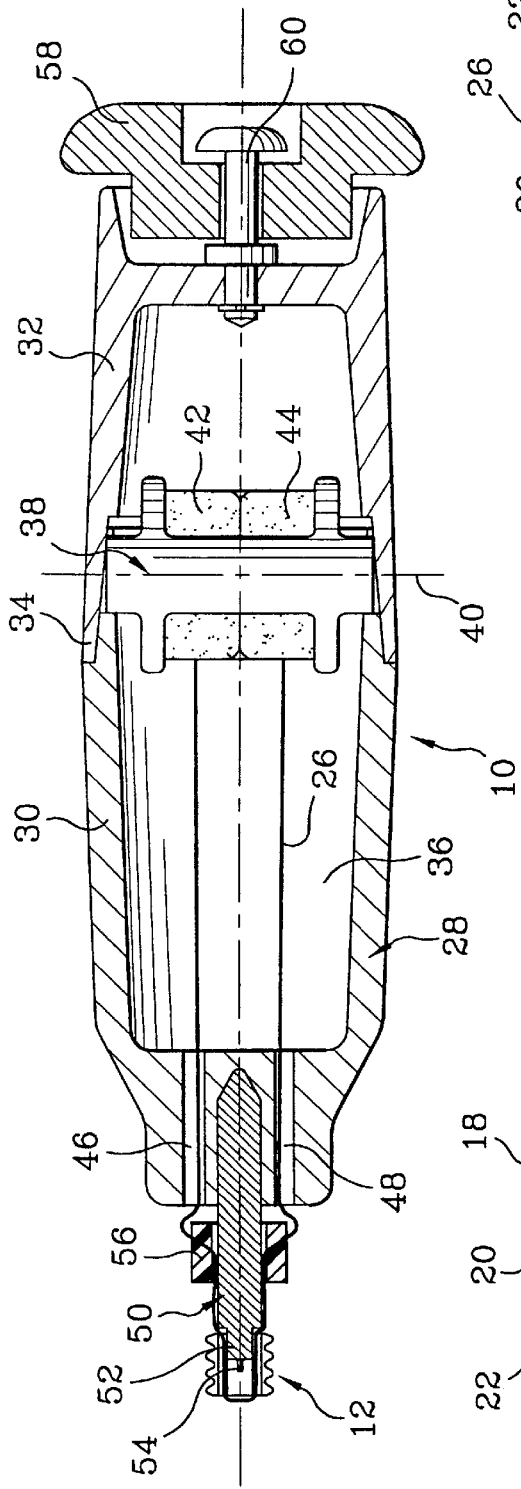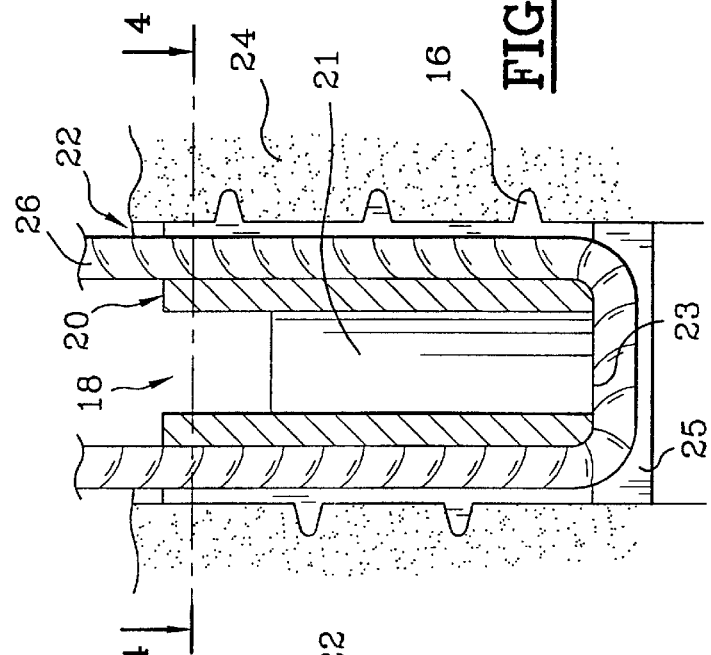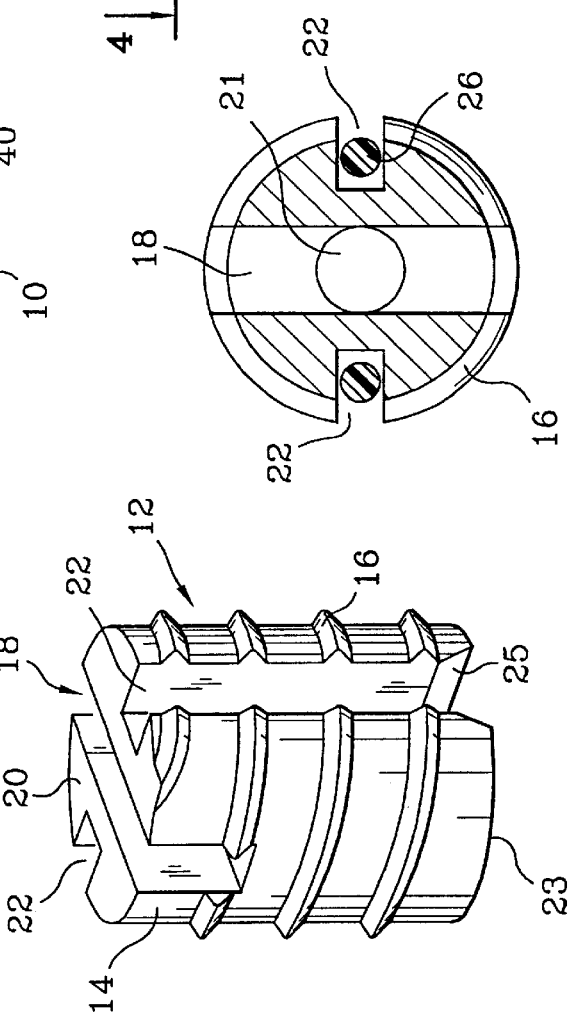

MEDICAL SCREW PARTICULARLY FOR SURGERY AND EMPLACEMENT TOOL

CROSS REFERENCE TO RELATED APPLICATION

This application corresponds to French application 96 08442 of Jul. 2, 1996, the disclosure of which is incorporated herein by reference.

FIELD OF THE INVENTION

The present invention relates to a medical screw usable particularly in cosmetic surgery so as to anchor a surgical suture as well as the emplacement tool. The invention also provides a modification.

BACKGROUND OF THE INVENTION

There are known screws having an anchoring function for medical-surgical use, particularly from U.S. Pat. No. 5,443,482, which discloses a self-tapping screw whose body is surmounted by a head forming an eyelet so as to permit the passage of a securement filament and even several securement filaments. The drawback of this screw is that it requires a tool difficult to provide and difficult to use. Moreover, the eyelet is of too great size given the surgical application in question.

There is also known from WO-A-93 15666 a screw pierced by a central open channel, the suture being in this case introduced through the channel and immobilized by knotting at the end of the channel. This screw has the advantage of having reduced size but the filament is premounted with a blocking knot and definitively immobilized once the screw is in place, there is therefore no possibility of sliding.

Another U.S. Pat. No. 5,411,523 discloses a screw which is provided to be anchored in the osseous cortical, this screw being surmounted by a manipulating rod made of one piece with the screw. This rod is provided with a rupture point at the screw/rod interface, so as to withdraw the rod when the screw is in place. The rod is moreover hollow and serves as a recess for storing the suture connected to this screw.

In addition to the production which will be understood to be difficult, two major drawbacks should be noted:

the filament is fixed and cannot slide, and the manipulating rod for screwing, once separated from the screw, cannot be used for unmounting.

U.S. Pat. No. 5,176,682 discloses a peg which has lateral anchors in the form of deformable tongues. These tongues are of one-piece with the body of the peg and are provided by suitable cutouts in the thickness of the body.

SUMMARY OF THE INVENTION

An internal screw is provided to be screwed axially in the body of said peg and the penetration of this screw gives rise to deformation of the tongues which project outside the body and anchor in the osseous material of the walls of a hole preliminarily provided to receive this peg. A modification provides a staple in place of the screw, the function being identical. It should be noted that withdrawal of the peg is quite difficult, even impossible.

Also, the present invention proposes a screw for surgical use, particularly to serve as anchoring of the securement of tendons and other ligaments, which is of reduced size, which is simple, which is produced independently of the tool, which permits sliding of the suture, which requires a particular tool which can easily be made for single use, and which is simple to use and quite natural for the practitioner with security as to guidance and positioning, the assembly also permitting removal.

The invention also relates to this particular tool.

To this end, the medical screw according to the invention, to anchor particularly in osseous material during surgery with the aid of a suture, with a screw body provided with at least one thread, provided to be screwed in a hole provided of substantially the diameter of the body, is characterized in that it comprises two longitudinal recesses to permit the free passage of the suture longitudinally in a loop below the screw and means to receive a tool to rotate it.

More particularly, the screw thread extends to the upper surface of the screw body to permit integral screwing of said body of the screw.

According to a preferred embodiment, the longitudinal recesses comprise two longitudinal grooves provided along the two opposite generatrices of the body of the screw, over all the length of the screw.

In this case, the means to receive a rotation tool comprise a transverse groove with a centering recess.

This tool comprises a screwdriver blade provided to coact with the transverse groove as well as means for storage and distribution of the filament.

Two modifications permit carrying it out with a spool or plates.

According to one modification, the longitudinal recesses are two longitudinal through holes, disposed along a diameter of the means to receive a rotating tool and comprise two longitudinal grooves along two opposite generatrices.

BRIEF DESCRIPTION OF THE DRAWINGS

The invention is described hereinafter with respect to the accompanying drawings which show a particular embodiment which is non-limiting, as well as a modification, the different figures showing:

FIG. 1, a cross-sectional view of a screw according to the invention and of the tool, FIG. 2, a perspective view of the screw according to the invention, FIG. 3, a cross-sectional view of a screw in place in the osseous cortical with the suture showing, FIG. 4, a cross-sectional view on the line 4—4 of FIG. 3, FIG. 5, a modified form of the screw, FIG. 6, a cross-sectional view on the line 6—6 of FIG. 5, FIGS. 7A and 7B, two views of emplacement of the suture in the case of the modification, with a particular threading of the filament, FIG. 8, a view of the end of the simplified tool, FIG. 9A, a longitudinal cross-sectional view of a modification of emplacement of the suture, and FIG. 9B, a longitudinal cross-sectional view perpendicular to that of FIG. 9A.

DETAILED DESCRIPTION OF THE INVENTION

Figure 5:
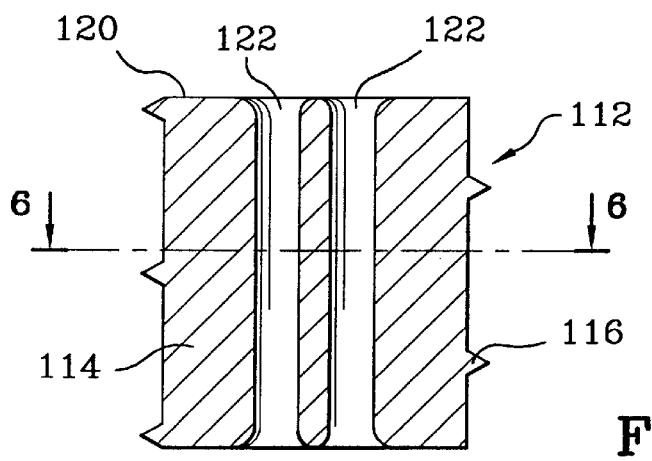
Figure 6:
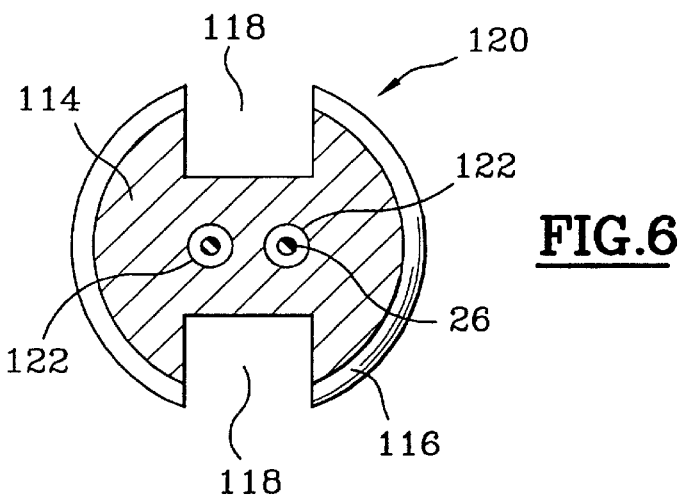
Figure 8:
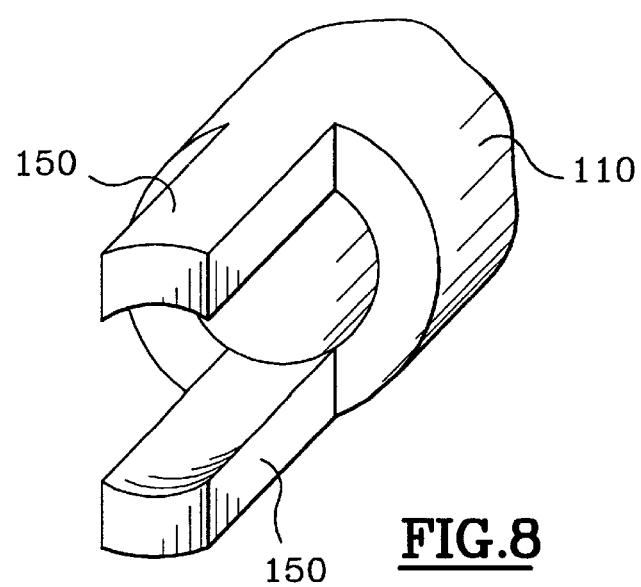

In FIG. 1 there is shown a tool 10 and a screw 12 according to the invention, in place on the tool.

In FIG. 2, the technical characteristics of the screw 12 of the invention will be better understood. Thus, this screw comprises a screw body 14, which is smooth, substantially cylindrical, and on the periphery of which is provided a screw thread 16.

An endwise open groove 18, transverse and diametral, is machined in the upper surface 20 of the screw, and has in a central part of the groove a hole 21, visible only in FIGS. 3 and 4.

At the two ends of the diameter perpendicular to the groove 18, there are two longitudinal grooves 22 machined along two generatrices. These two grooves are perfectly smooth so as not to present any sharp surfaces.

Referring to FIGS. 3 and 4, there will be seen the screw implanted in the osseous material 24, the screw threads 16 penetrating the osseous material in known manner.

The surgical filament 26 passes through one of the longitudinal grooves 22, and beneath the lower surface 23 of the screw, and leaves by the other longitudinal groove 22. The lower surface 23 is provided with a groove 25, for example of V shape, so as to facilitate the guidance of the filament and to permit sliding of said filament even if the screw is at the bottom of the hole during emplacement.

It will be understood that the filament could slide freely between the osseous wall and the bottom of each of the grooves 22.

Emplacement is carried out with a tool 10 shown in cross section in FIG. 1, which tool comprises a hollow body 28 made of two parts, a lower part 30 and an upper part 32, and provided to be secured together substantially at the middle of the hollow body, at 34. The hollow body comprises, once assembled, a free internal volume 36, in which is disposed a spool 38 mounted for rotation transversely relative to the longitudinal axis of the hollow body, about the axis 40. This spool comprises two windings 42 and 44 of suture 26. At the lower end of the lower portion of the hollow body, there are provided two holes 46, 48 through which pass the two lengths of suture 26.

The lower portion 30 is prolonged by a screwdriver blade 50 whose end 52 is provided to coact with the groove 18. This end 52 carries particularly a cylindrical centering projection 54 adapted to penetrate the hole 21 provided in the central portion of the groove 18.

A ring 56, with a slot in its middle portion, to serve for guidance and orientation, is mounted coaxially to the screwdriver blade 50, the runs of the suture 26 passing necessarily between the exterior of the screwdriver blade and the interior of said ring so as to ensure guidance. It will also be noted that the ring 56 permits pulling the surgical filament, disposing it against the screwdriver blade so that it will be disposed at the bottom of the longitudinal grooves 22, the filament remaining protected during emplacement of the screw.

The upper end of the upper portion 32 is surmounted by a knob 58 freely mounted rotatably on an axle 60.

The tool, of the disposable type, is hence preferably of plastic material for obvious reasons of cost, the screw itself being made of a light alloy, biocompatible, for example of titanium or titanium alloy.

Thus, the screw and tool assembly is sold premounted.

It suffices for the practitioner to pierce with a drill having substantially the diameter of the body of the screw, at the bottom of the screw thread, then to insert the screw held on the end of the tool, to position the screw at the inlet of the hole by pressing on the rotor to exert a penetrating force with simultaneously rotation of the hollow body 28 of the tool. This rotation is transmitted to the screw by the screwdriver blade.

The practitioner exerts rotation until the screw has completely penetrated the hole, then he withdraws the tool and it is only at this time that the filament rolled up on the spool unrolls. The tool can then be put aside until the end of the operation.

The surgeon proceeds to secure the biological ligament element, tendon or muscle with the possibility of being able to slide the filament and to adjust completely its position. The screw itself is completely integrated into the osseous material without any projecting element.

In the case of error of manipulation, the surgeon is also able to withdraw the screw and the suture attached thereto. It suffices to replace the tool, this operation being simplified by good accessibility of the groove 18 on the upper surface 20 of the screw and thanks to the centering projection 54 which penetrates the hole 21.

It will also be noted that the screw thread 16 is interrupted in line with each of the longitudinal grooves 22 forming tappings and thus facilitating the penetration and positioning of the screw. This good penetration of the screw threads into the osseous material ensures excellent anchoring.

A modification of the invention is shown in FIGS. 5, 6, 7A, 7B and 8. For reasons of simplification and for comparison of the two modifications, the references relating to identical elements or elements having the same function bear the same reference numbers increased by 100.

The screw 120 of this modification comprises two holes 122 provided for the passage of the filament 26. These two holes are disposed along a first diameter, and along a second perpendicular diameter there are provided two longitudinal grooves 118 provided to receive the screwing lugs 150 of a tool 110.

The screw thread 116 is substantially identical to the preceding screw thread 16.

Figure 7A:
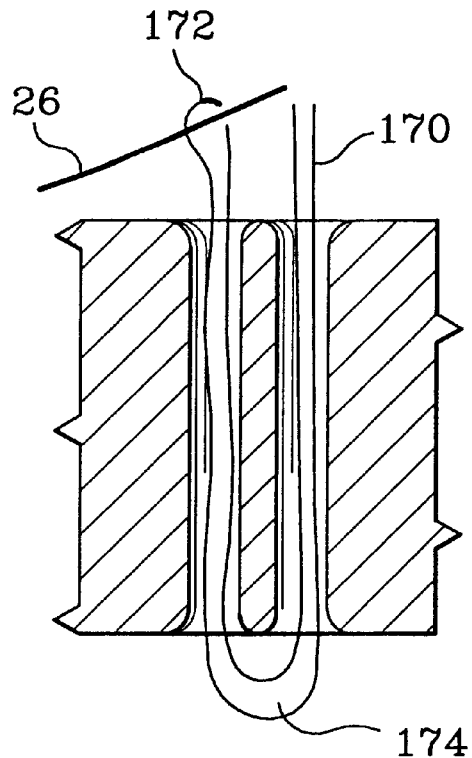

In this modification, the tool 110 contains no filament and the screw contains a premounted sling 170, which is only a metallic filament for example, of small cross section and of such shape as to penetrate via a hole 122 and emerge from another hole 122, as indicated in FIG. 7A. The sling is doubled so as to form a loop 172.

Figure 7B:
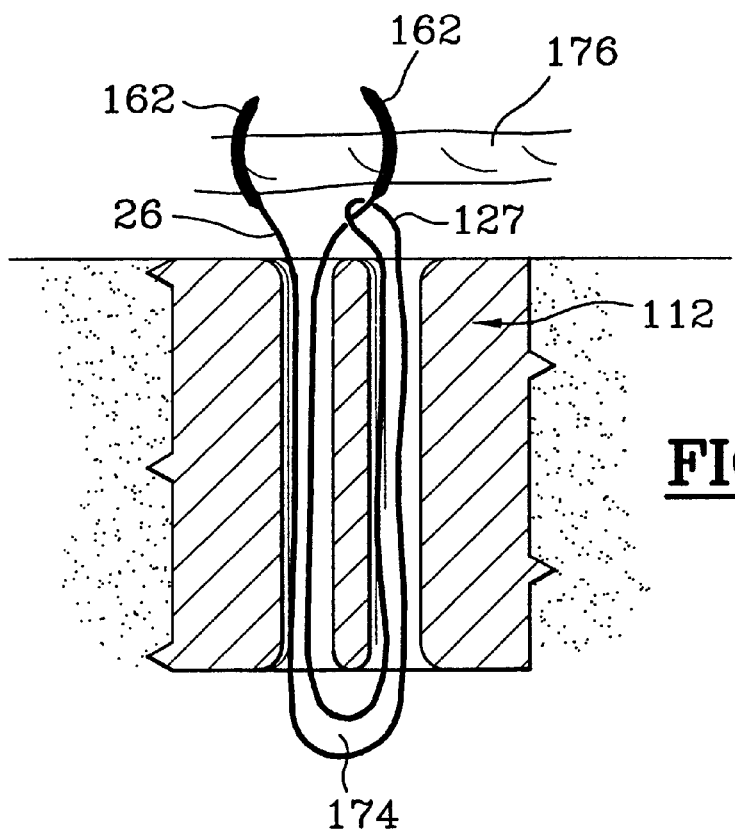

FIGS. 7A and 7B show the introduction and use of a suture 26 provided with a needle 162 at each of its ends, with the screw according to this modification.

After screwing the screw into a hole provided in known fashion with the aid of a drill, it suffices to introduce the suture 26 into the loop 172 and to pull on the sling by its two free ends simultaneously. The suture then follows the sling and is introduced in its turn into the two holes 122 by passing below the screw 112 in the form of a loop 174.

The practitioner does the same to secure element 176, on this anchor by means of the filament 26. It suffices for him to punch with one of the needles 162 the element to be secured passing through it, then to pass the second run with its needle into the loop 127 of the filament 26 before securing the second run to the element 176, to complete the securement operation. This particular path of the filament can of course be used in the principal embodiment.

The practitioner can also cause a single filament to pass and to ensure the connection in known manner, the loop arrangement being but a suitable way to connect the filaments.

It should again be noted that the filament can slide to be adjusted in position before or during emplacement of the element 176. The size is reduced as in the preceding case and the element can be applied without damage to the bone, in line with the screw because no element protrudes.

The emplacement tool is even simpler to make with the possibility of using a sling and with the advantage of being able to choose at the last moment the type of filament, but this modification of screw can of course be provided to be premounted with a given suture.

It should also be noted that the emplacement of the screw is easy thanks to good guidance by the tool.

Figures 9A, 9B:
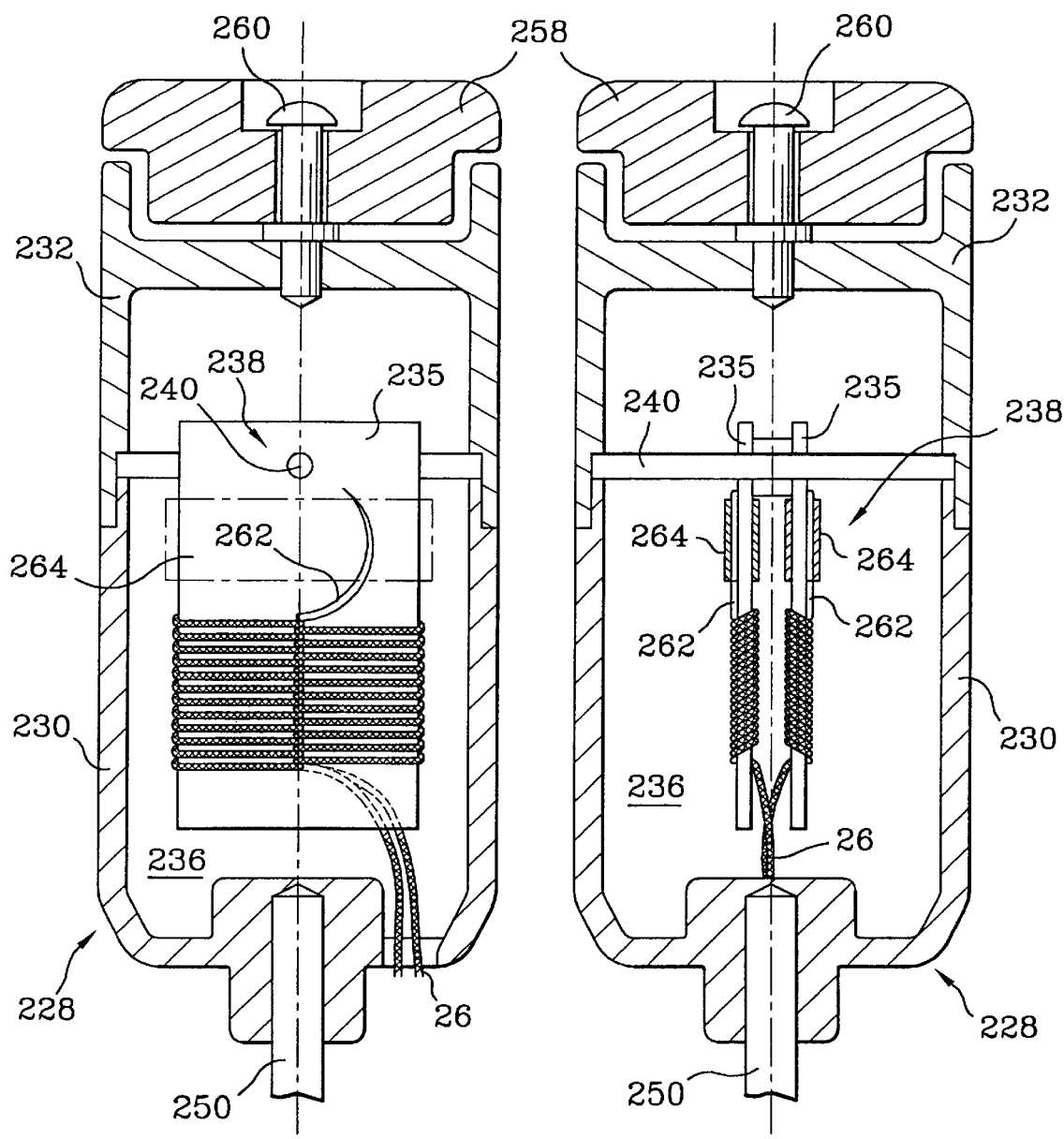

In FIGS. 9A and 9B, there is shown a modification of the tool, elements that are identical or having the same function being given the same reference numerals increased by 200.

Only the rotatable spool is replaced by two plates 235 on which are rolled the free lengths of filament 26. Each plate is provided with a slot in which the suture 26 is caught.

A pivotal axle 240 permits good orientation of the plates 235, particularly during unwinding of the filament.

It will also be noted that in this modification, it is possible to arrange needles 262 at each of the ends of the filament without disturbing the unwinding of the filament. These needles are maintained by elastic sleeves 264 on the plates 235.

What is claimed is:

1. Medical screw for anchoring in osseous material during surgery to secure a suture, comprising:

a screw body extending in a direction along a longitudinal axis from a first end to an opposite second end, and having an outer peripheral surface;

a screw thread extending radially from said outer peripheral surface relative to said longitudinal axis;

said outer peripheral surface comprising a first and second longitudinal grooves provided along two opposite generatrices of said screw body;

said first and second longitudinal grooves extending from said first and to said opposite second end to permit free passage of the suture longitudinally in a loop around an end of the screw; and means on the screw body for receiving a tool to rotate the screw body.

2. Medical screw according to claim 1, further comprising a third groove which extends at said opposite second end from said first groove to said second groove in a first transverse direction relative to said longitudinal axis.

3. Medical screw according to claim 1, wherein the screw thread extends to the first end of the screw body.

4. Medical screw according to claim 2, further comprising a fourth groove which extends at said first end in a second transverse direction relative to said longitudinal axis, said first transverse direction being perpendicular to said second transverse direction.

* * * * *